(12) United States Patent
Burnett et al.

(10) Patent No.: US 7,347,868 B2
(45) Date of Patent: Mar. 25, 2008

(54) MEDICAL DEVICE DELIVERY CATHETER

(75) Inventors: Daniel R. Burnett, San Francisco, CA (US); Gregory W. Hall, Redwood City, CA (US); Jordan T. Bajor, Palo Alto, CA (US); Winfield Scott Fisher, Alameda, CA (US); Tibor Laszlo Hites, Lafayette, CA (US)

(73) Assignee: BAROnova, Inc., Goleta, CA (US)

( * ) Notice: Subject to any disclaimer, the term of this patent is extended or adjusted under 35 U.S.C. 154(b) by 486 days.

(21) Appl. No.: 10/974,482

(22) Filed: Oct. 26, 2004

(65) Prior Publication Data

US 2006/0089627 A1    Apr. 27, 2006

(51) Int. Cl.
*A61F 2/06* (2006.01)

(52) U.S. Cl. ..................... 623/1.11; 606/198

(58) Field of Classification Search ...... 623/1.11–2.11, 623/23.64–23; 606/198
See application file for complete search history.

(56) References Cited

U.S. PATENT DOCUMENTS

| | | | |
|---|---|---|---|
| 5,222,970 A * | 6/1993 | Reeves | ........................ 606/195 |
| 5,423,872 A | 6/1995 | Cigaina | |
| 5,820,584 A | 10/1998 | Crabb | |
| 6,183,520 B1 | 2/2001 | Pintauro et al. | |
| 6,409,656 B1 | 6/2002 | Sangouard et al. | |
| 6,488,962 B1 | 12/2002 | Berner et al. | |
| 6,540,789 B1 | 4/2003 | Silverman et al. | |
| 6,544,291 B2 | 4/2003 | Taylor | |
| 6,558,400 B2 | 5/2003 | Deem et al. | |
| 6,669,719 B2 * | 12/2003 | Wallace et al. | ............. 623/1.12 |
| 2002/0188354 A1 | 12/2002 | Peghini | |
| 2003/0023150 A1 | 1/2003 | Yokoi et al. | |
| 2003/0040804 A1 | 2/2003 | Stack et al. | |
| 2003/0078611 A1 | 4/2003 | Hashiba et al. | |
| 2003/0093117 A1 | 5/2003 | Saadat | |
| 2003/0109931 A1 | 6/2003 | Geitz | |
| 2003/0109935 A1 | 6/2003 | Geitz | |
| 2003/0144708 A1 | 7/2003 | Starkebaum | |
| 2003/0153806 A1 | 8/2003 | Miller | |
| 2003/0158601 A1 | 8/2003 | Silverman et al. | |
| 2004/0117031 A1 * | 6/2004 | Stack et al. | .............. 623/23.65 |

FOREIGN PATENT DOCUMENTS

| WO | WO 02/091961 A1 | 11/2002 |
|---|---|---|
| WO | WO 03/017882 A2 | 3/2003 |

\* cited by examiner

*Primary Examiner*—Suzette Gherbi
(74) *Attorney, Agent, or Firm*—K. David Crockett, Esq.; Crockett & Crockett

(57) ABSTRACT

Apparatus for delivering a medical device to a location in a patient's body includes an elongate catheter body having a proximal end and a distal end, a pod coupled with the distal end of the catheter body and adapted to house the medical device during delivery to the location and to open to release the medical device, and at least one distal actuator coupled with at least one of the pod and the medical device. The distal actuator is adapted to promote opening of the pod. A method involves advancing a pod at the distal end of an elongate catheter to the location within the body and activating an actuator coupled with the pod and/or the medical device to cause the pod to open. Opening the pod releases the medical device.

26 Claims, 5 Drawing Sheets

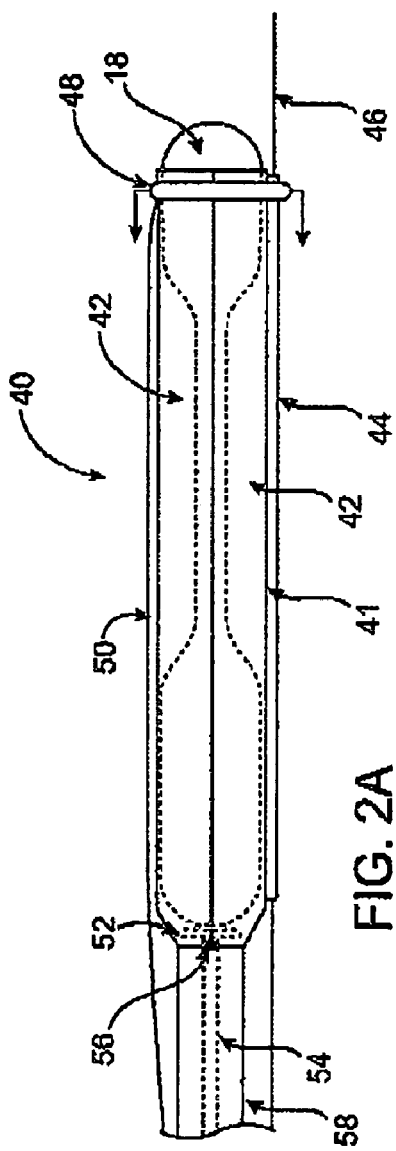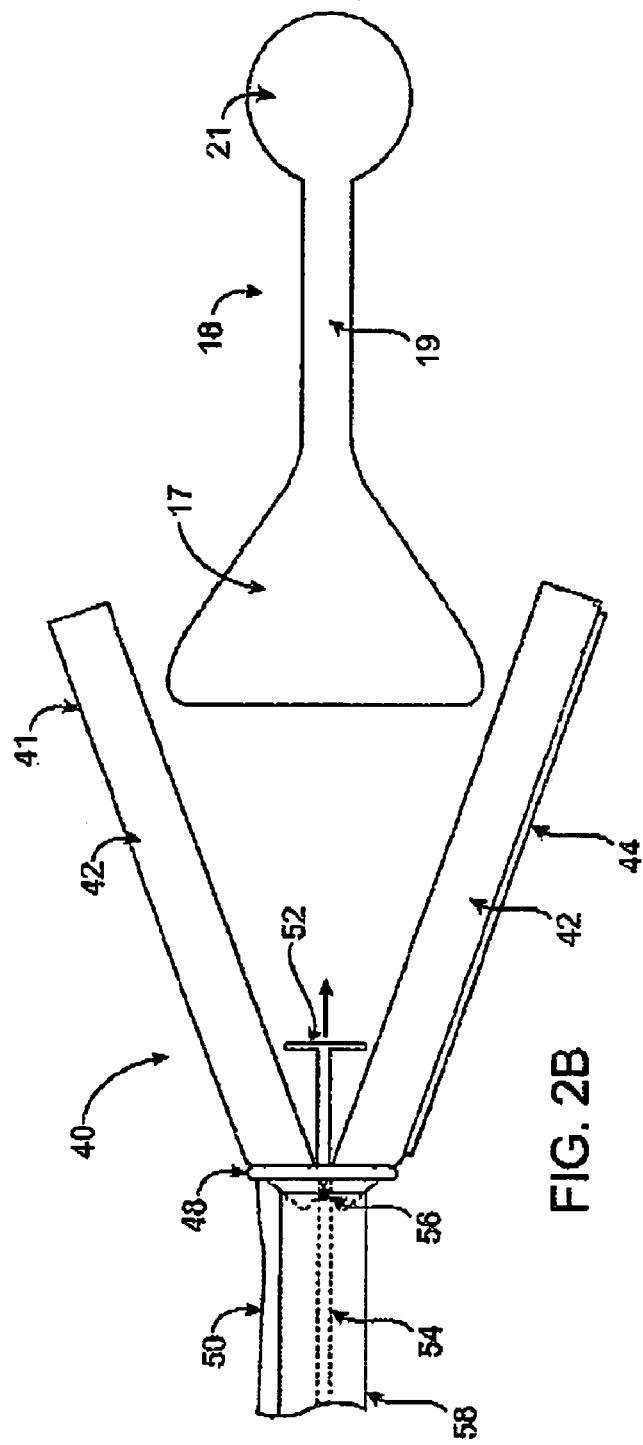

MEDICAL DEVICE DELIVERY CATHETER

CROSS REFERENCE TO RELATED APPLICATIONS

This application is related to U.S. patent application Ser. Nos.: 10/671,191 filed Sep. 24, 2003; 10/833,950 filed Apr. 27, 2004; and 10/915,716 filed Aug. 9, 2004, the full disclosures of which are all hereby incorporated by reference.

BACKGROUND OF THE INVENTION

The present invention relates generally to medical devices and methods. More specifically, the invention relates to catheter devices and methods for delivering a medical device to a location within a patient's body.

One of the most pervasive trends in modern medicine and surgery is the development of devices and methods for performing minimally invasive procedures. For example, balloon angioplasty and stent placement are techniques that were developed as alternatives to open heart, coronary artery bypass procedures. Arthoscopic surgical procedures have been developed in orthopedics for performing various surgical procedures on the knee, shoulder and other joints through small incisions, thus avoiding traditional, open surgical techniques. Laparoscopic surgical procedures have been developed for gall bladder removal and other intra-abdominal surgeries, to reduce trauma and speed recovery time by requiring only small incisions and minimal abdominal wall trauma. Developments in the minimally invasive arena have even evolved toward robotic surgical systems, such as the da Vinci® Surgical System provided by Intuitive Surgical, Inc. (Sunnyvale, Calif.), which allows a surgeon to remotely perform operations ranging from prostate or gall bladder removal to coronary bypass. Hundreds, if not thousands, of new minimally invasive techniques are still being developed. For example, a number of established and start-up medical device companies are developing techniques for repairing or replacing heart valves, ablating portions of the heart to treat arrhythmias, and performing other cardiac procedures using catheter-based devices.

Other examples of a minimally invasive procedures, devices and systems are described in U.S. patent application Ser. Nos.: 10/671,191, 10/833,950 and 10/915,716, which were incorporated by reference immediately above. Generally, these methods and devices involve placing a device in a patient's stomach (and sometimes placing a portion of the device across the pyloric valve of the stomach in the duodenum) to treat or ameliorate obesity and/or to perform any of a number of other functions, such as to help treat other gastrointestinal disorders.

Many of the newly developed minimally invasive techniques, and many that will be developed in the future, involve using a catheter device to deliver a therapy within a patient's body. Some techniques, such as placing stents in a coronary artery to prop open the artery, involve delivering a medical device (in this case a stent) from the distal end of the catheter. In another example, a device may be placed into the stomach and/or the duodenum via a catheter advanced through the patient's esophagus. In many cases, delivering medical devices to locations within the body using a long, flexible catheter may be difficult or awkward. For example, it may be difficult to sufficiently control advancement of a long, flexible, low-profile catheter to position a distally-housed medical device in a desired location in the body. Even once the distal end of the catheter is advanced to a desired position, it may be difficult to release the medical device from the catheter in precisely the desired location and orientation. Releasing the device may even damage the device and/or nearby delicate human tissue, in some cases.

For example, delivering a medical device via an elongate catheter often involves sliding the device out of the catheter. Friction between sliding surfaces of the medical device and the delivery catheter complicates delivery of the device, especially when the catheter is curved to follow a tortuous pathway, such as a coronary blood vessel. In the case of stent delivery, for example, stent delivery from the distal end of a delivery catheter typically involves pushing the stent out of the catheter and/or retracting the catheter proximally relative to the stent, while holding the stent in place, all actions which may damage the stent. Furthermore, a stent is compressed or collapsed to fit within the catheter, thus storing energy in the stent. When the stent is released, the stored energy may often cause it to propel forward to an undesired location. Additionally, such a delivery catheter requires a pusher device for pushing the stent out or holding it stable while a portion of the catheter is retracted and/or a retractable sheath or sleeve, both of which complicate manufacturing of the delivery device and necessitate a larger delivery device profile. Catheter-based delivery of other medial devices to various locations in the body, such as placing a device in the stomach, pyloric valve and/or duodenum, may face similar challenges.

Therefore, a need exists for effective, minimally-invasive or non-invasive devices and methods for delivering medical devices within a patient's body. Ideally, such devices and methods would be relatively easy to use and allow for atraumatic delivery of a medical device to a desired location without damaging the medical device or the delivery device. Also ideally, such delivery devices would be relatively low-profile and allow for precise device placement at the desired location in the body. At least some of these objectives will be met by the present invention.

BRIEF SUMMARY OF THE INVENTION

The present invention provides apparatus, systems and methods for delivering a medical device to a location in a patient's body. In one aspect of the present invention, apparatus for delivering a medical device to a location within a patient's body includes an elongate catheter body having a proximal end and a distal end, a pod coupled with the distal end of the catheter body and adapted to house the medical device during delivery to the location and to open to release the medical device, and at least one distal actuator coupled with at least one of the pod and the medical device, the distal actuator adapted to promote opening of the pod.

In some embodiments, the pod comprises a material disposed over the medical device, and the material is adapted to tear or peel to open the pod. For example, such a material may be either resilient or rigid in various embodiments, such as but not limited to silicone, polyisoprene, polyimide, polyurethane, polyolefin, polyethylene, nylon, latex, neoprene, stainless steel, nitinol, ceramic, Teflon, a biodegradable material, composites or the like. In some embodiments, the material comprises a shape-memory material adapted to curl inward after the material is torn or peeled. Alternatively, the material may include at least one set of perforations or slits to promote tearing or peeling of the material. The perforations may be disposed along the pod in any suitable configuration, such as in a straight line(s) parallel to a long axis of the pod, straight line(s) circumferential about and perpendicular to the long axis of the pod, spiral line(s), wavy line(s) or lines forming an open-mouth shape. In yet another embodiment, the material includes a plurality of apertures disposed along opposite ends, and the apparatus further includes a cord for passing through the apertures to maintain the material over the medical device. Removing the cord causes the pod to open. Alternatively, the material may include at least one structurally weaker portion, relative to the rest of the material, to promote tearing or peeling of the material. In still other embodiments, the material includes at least one zip-lock member along at least part of its length, the zip-lock member adapted to unzip from a closed, locked configuration to an open configuration.

In some embodiments, the distal actuator is adapted to cut the material, and the actuator may include any suitable cutter, such as one or more blades, rip cords, wires, threads, wedges, other cutting members or zippers. In other embodiments, the distal actuator comprises a pressure input member for introducing positive pressure into the pod to cause the material to burst. Alternatively, the distal actuator may comprise an inflation device coupled with the medical device for inflating the medical device to cause the device to expand and rupture the material.

In some embodiments, the apparatus further includes a retractable inner shaft extending axially through the housing. The medical device includes at least one lumen to allow the medical device to reside over the inner shaft during delivery, such that retracting the inner shaft releases at least part of the medical device. For example, in some embodiments, the retractable shaft extends beyond a distal end of the pod, and retracting the shaft releases a distal portion of the medical device, while opening the pod releases a proximal portion of the medical device.

In an alternative embodiment, the pod comprises at least two opposed housing members for releasably housing the medical device and at least one hinge for movably coupling the housing members. The housing members are adapted to move about the hinge(s) to cause the pod to open. The housing members, for example, may comprise a material such as but not limited to a polymer, a ceramic, a metal, a composite or a biological material. In various embodiments, the hinge may be a flexible material hinge, a living hinge, a pin joint, a universal joint or any other hinge or joint. In some embodiments, at least part of each housing member comprises a shape-memory material, a super-elastic material or a spring loaded material, and the housing members are preformed to move away from one another when released from constraint. In some embodiments, the distal actuator is adapted to releasably hold the pod in a closed configuration and, upon activation, to release the pod to allow it to assume the open configuration. Such distal actuators may include, for example, a ring, a retractable sleeve, a tearable sleeve, a pin or a clamp.

Some embodiments of the apparatus further include at least one spring disposed between the housing members to urge them apart. The distal actuator may comprise at least one movable holder disposed about the housing members, and the holder is movable from a first position to hold the housing members together to a second position to allow the housing members to move apart. Optionally, the holder may be movable from the second position to the first position to move the housing members back together. In some embodiments, the holder comprises at least one ring disposed around the housing members. The ring in the first position is disposed near a distal end of the pod and the ring in the second position is disposed near a proximal end of the pod. Alternatively, the holder may comprise a sleeve movably disposed over the housing members. In some embodiments, the actuator further comprises a wedge for urging the housing members apart when the holder is moved from the first to the second position.

Additional features may also be included. For example, the pod may include at least one radiopaque marker or material. Various embodiments may have pods with different tip configurations. For example, the pod may have an open distal end or a closed distal tip. A tip, in some embodiments, may be a rigid, pointed tip adapted to pierce through tissue. Alternatively, the tip may be a blunt, atraumatic tip to prevent tissue damage during advancement of the pod. In some embodiments, the tip includes flexible nose having at least one aperture or lumen for accepting a guidewire.

Optionally, the apparatus may also include a movable pusher member disposed in the pod to urge the medical device out of the opened pod. For example, the pusher member may include a platform disposed near a proximal end of the pod for contacting and urging the medical device and an elongate shaft coupled with the platform and extending through the catheter body to its proximal end to allow a user to advance and retract the platform. In another embodiment, the pusher member comprises a spring-loaded platform disposed near a proximal end of the pod, the platform adapted to urge the medical device out of the pod upon release from constraint. In some embodiments, the platform is automatically released from constraint when the pod opens. In other embodiments, the platform is released from constraint by the user. The apparatus may also include a safety mechanism releasably coupled with the platform to prevent the platform from advancing prematurely.

Some embodiments of the device further include at least one support member disposed along at least part of a length of the pod for reducing bending of the pod. In one embodiment, for example, multiple support members are disposed along an inner surface of the pod. Such support members may comprise silicone or any other suitable material. The apparatus may also include a guidewire lumen disposed along at least part of the pod. Such a guidewire lumen may be disposed along an outer surface of the pod or an inner surface of the pod. In some embodiments, the guidewire lumen extends onto at least part of the catheter body. Optionally, an additional guidewire lumen may be disposed along at least part of the medical device.

In some embodiments, the device includes at least one proximal actuator coupled with the distal actuator to allow a user to activate the distal actuator. Such a proximal actuator may include, for example, a trigger, a pull cord, a button, a dial, a slide actuator or the like. In some embodiments, the proximal actuator is coupled with the distal actuator via at least one of a shaft and a cord extending through a lumen of the catheter body. Alternatively, the proximal actuator may be coupled with the distal actuator via an electrical connection. Optionally, the catheter body may include a series of depth markings on its outer surface to indicate to a user how far the pod is inserted within the patient's body.

In one embodiment, the medical device is adapted to reside in a stomach and intermittently contact a pyloric valve. For example, one device includes a distal portion for residing in a duodenum, a proximal portion for residing in the stomach, and an elongate connecting portion for connecting the distal portion with the proximal portion and adapted to extend across the pyloric valve. In some embodiments, the delivery apparatus is adapted to release the distal portion in the duodenum and then release the proximal portion in the stomach. Also in some embodiments, the medical device is adapted to slow the passage of food from through the pyloric valve to help treat obesity. Alternatively, or additionally, the medical device may adapted to house or anchor a second medical device disposed in the stomach, a small intestine or both to perform a function within the stomach and/or small intestine.

In another aspect of the present invention, apparatus for delivering a medical device to a location in a patient's body includes an elongate catheter body having a proximal end and a distal end, and a pod coupled with the distal end of the catheter body and adapted to house the medical device during delivery to the location and to open to release the medical device. The pod is adapted to automatically open after being positioned in the location. In one embodiment, the pod comprises a material disposed over the medical device, and at least part of the material is biodegradable. Optionally, the pod may further include at least two opposed housing members disposed within the material, wherein the housing members automatically move apart to cause the pod to open when the material at least partially degrades. In some embodiments, the location is a stomach of the patient, and at least part of the material is rapidly biodegradable in the stomach. In alternative embodiments, the pod comprises a material disposed over the medical device, and at least part of the material degrades upon reaching a temperature present at a desired delivery location.

In another aspect of the present invention, a system for delivering a medical device to a location in a patient's body includes an elongate catheter body having a proximal end and a distal end, a pod coupled with the distal end of the catheter body and adapted to house the medical device during delivery to the location and to open to release the medical device, at least one distal actuator coupled with at least one of the pod and the medical device, the distal actuator adapted to promote opening of the pod, and a medical device releasably housed within the pod. In some embodiments, the device includes a distal portion for residing in a duodenum, a proximal portion for residing in the stomach, and an elongate connecting portion for connecting the distal portion with the proximal portion and adapted to extend across the pyloric valve. The delivery apparatus may be adapted to release the distal portion in the duodenum and then release the proximal portion in the stomach. In one embodiment, the medical device is adapted to reside in a stomach and intermittently contact the pyloric valve. Such a medical device may be adapted to slow the passage of food from through the pyloric valve to help treat obesity. Alternatively, or additionally, the medical device may be adapted to house or anchor a second medical device disposed in the stomach, a small intestine or both to perform a function within the stomach and/or small intestine. In one embodiment, the system further includes a tether coupling the medical device to at least one of the catheter body and the pod. Removing the catheter from the patient removes the medical device from the patient.

In yet another aspect of the present invention, a method for delivering a medical device to a location in a patient's body includes advancing a pod at the distal end of an elongate catheter to the location within the body and activating an actuator coupled with at least one of the pod and the medical device to cause the pod to open. Opening the pod releases the medical device. In some embodiments, at least a distal portion of the pod is advanced across the patient's pyloric valve, such that when the pod is opened, a distal portion of the medical device resides in the patient's duodenum, a proximal portion of the device resides in the patient's stomach, and an elongate connecting portion extends between the distal and proximal portions, across the pyloric valve.

In some embodiments, activating the actuator comprises at least one of tearing, peeling and cutting the pod. For example, in various embodiments the pod may be torn, peeled or cut along one or more perforated lines or lines of structural weakness. Activating the actuator, in one embodiment, involves withdrawing a cord from a plurality of apertures in the pod, the cord adapted to hold the pod together around the medical device. Alternatively, activating the actuator may involve retracting a sleeve disposed over shape-memory, super-elastic or spring loaded housing. In another embodiment, activating the actuator comprises retracting a ring disposed over two or more housing members of the pod, wherein the housing members automatically move apart when released from constraint within the ring. In yet another alternative, activating the actuator may involve pressurizing the pod to cause it to burst open. Or, activating the actuator may involve inflating the medical device to cause it to expand and thus burst open the pod.

In some embodiments, the method further comprises urging the medical device out of the opened pod with a pusher member. The method may also include retracting an inner shaft extending through a longitudinal lumen of the medical device, wherein retracting the shaft releases at least a portion of the device. In one embodiment, the released portion of the medical device comprises a distal shape-memory portion configured to change from a straight configuration when disposed over the shaft to a non-linear configuration when released from the shaft. In some embodiments, the pod is advanced over a guidewire extending through a guidewire lumen on the pod.

These and other aspects and embodiments of the invention are described in greater detail below, with reference to the attached drawing figures.

BRIEF DESCRIPTION OF THE DRAWINGS

FIGS. 2A and 2B are side views of a distal end of a medical device delivery catheter in closed (FIG. 2A) and open (FIG. 2B) configurations, according to one embodiment of the present invention.

DETAILED DESCRIPTION OF THE INVENTION

In various embodiments, a medical device delivery catheter may be used to delivery any of a number of medical devices in any of a number of locations in a human body. For example, one embodiment may be used to deliver stents in an a coronary artery, another embodiment may deliver stents in peripheral blood vessels, other embodiments may be used to deliver various devices within the heart, orthopedic embodiments may be used to deliver devices within various joints, and the like. In the description that follows and in the attached figures, various embodiments of a medical device delivery catheter are adapted for delivering a device in a patient's stomach, with the device in some cases crossing the pyloric valve and extending into the duodenum. Examples of such devices are described in U.S. patent application Ser. Nos.: 10/671,191, 10/833,950 and 10/915,716, which are assigned to the assignee of the present invention and which were previously incorporated by reference. Alternative embodiments, however, may be used for delivering any other suitable device to any of a number of locations in the body.

Figure 1:
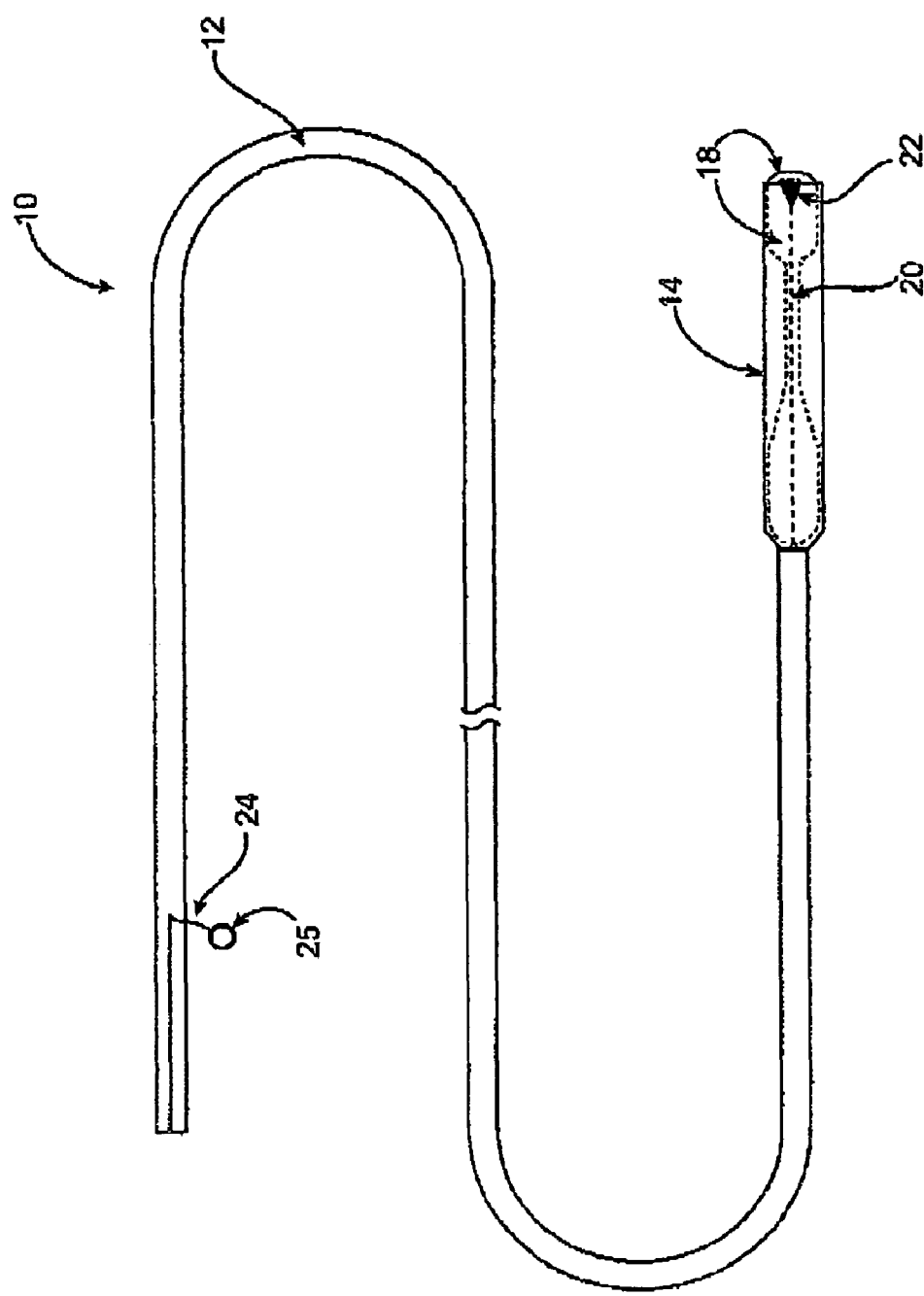
FIG. 1 is a perspective view of a medical device delivery catheter, according to one embodiment of the present invention.

That being said, and referring now to FIG. 1, in one embodiment, a medical device delivery catheter 10 includes a catheter body 12 with a peel-away pod 14 at its distal end. A medical device 18, in this embodiment a device for placing in a stomach, is housed within peel-away pod 14. Peel-away pod 14 includes perforations 20 and a cutter 22. A pull cord 24 is attached to cutter 22 and extends through catheter body 12 to exit proximally and attach to a pull ring 25. Pulling proximally on pull ring 25 causes cutter 22 to move proximally along perforations 20, thus opening peel-away pod 14 to release medical device 18.

In various embodiments, peel-away pod 14 may cover all or only part of medical device 18 during delivery. Pod 14 may generally be made of any of a number of different materials or combinations of materials. Typically, peel-away pod 14 is made of a resilient or elastomeric material that is positioned, sometimes stretched, over medical device 18. Such resilient materials may include, for example, silicone, polyisoprene, polyimide, polyurethane, polyolefin or the like. In alternative embodiments, peel-away pod 14 may be made of a rigid material such as but not limited to polyethylene, nylon, stainless steel, nitinol, ceramic, Teflon or a composite material, with perforations 20, slits, holes or the like allowing pod 14 to break or tear apart. Perforations 20 extend along the entire length of pod 14 or only part of pod 14. They may also be disposed along pod 14 in any suitable configuration or pattern, such as in one or more longitudinal lines, one or more circumferential lines, one or more spiral lines, an open mouth configuration, irregular or asymmetrical patterns, or the like. In yet other embodiments, one or more lines of structural weakness, other than perforations 20, may be built into peel-away pod 14, such as lines of thinner or structurally weaker material, a non-reinforced portion of a pod 14 that is reinforced elsewhere via fibers, bands or the like, or a combination of non-homogeneous materials.

In alternative embodiments, all or part of pod 14 may be made of a biodegradable material adapted to dissolve upon positioning within the desired delivery location, thus releasing medical device 18. For example, pod 14 may be made of a material designed to rapidly dissolve within the environment of the stomach. Examples of such biodegradable materials include, but are not limited to, gelatin, wax, starch, lactic acid, sugars, proteins, gum and polyvinyl alcohol. Some non-degradable pods 14 may be made of shape-memory or super-elastic material such that they curl or fold inward after they are torn or peeled open to release medical device 18. Curling over edges of pod 14 may help prevent damaging contact with tissues during extraction of delivery device 10.

Figure 6:
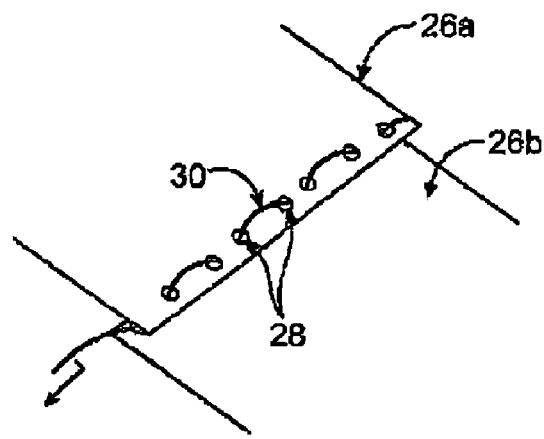
FIG. 6 is a perspective view of a portion of a material for forming a pod, illustrating one method for coupling edges of the pod material together, according to one embodiment of the present invention.

Any of a number of suitable mechanisms may be used to allow pod 14 to open via tearing, peeling, splitting, or the like. Perforations 20 are but one example. As shown in FIG. 6, in other embodiments, a pod material 26 may have multiple apertures 30 in opposite edges 26a, 26b, such that material 26 may be wrapped around a medical device (not shown) and the edges 26a, 26b may be attached via a cord 30. (Generally, for the purposes of this application, the term "cord" shall mean any cord, wire, thread, filament, string or the like.) Cord 30 is wound through apertures 28 to hold the two edges 26a, 26b of material 26 together, thus constraining medical device 18 within material 26. Cord 30 may then be withdrawn (solid-tipped arrow) to free edges 26a, 26b, thus allowing material 26 to open, and thus releasing the medical device. In various embodiments, cord 30 may be sewn through apertures 28 or perforations or wrapped or looped around apertures 28 or perforations.

Returning to FIG. 1, in various embodiments, any suitable cutter 22 or other actuator device for cutting or beginning a tear in peel-away pod 14 may be used. For example, cutter 22 may be a blade, cord, wedge, or the like. In an alternative embodiment, part of medical device 18 itself may act as cutter 22, with that part of medical device 18 being retracted or advanced in such a way as to cut pod 14. Alternatively, a zipper may be used to unzip peel-away pod 14. In one embodiment, perforations 20 are replaced with a zip-lock device, which is unzipped to open pod 14.

Cutter 22 is attached to pull cord 24, which extends from cutter 22 through catheter body 12 to exit proximally and attach to pull ring 25. In various alternative embodiments, pull ring 25 may be replaced with any other actuator devices, such as but not limited to a slide, trigger, button or the like. Pulling proximally on pull ring 25 moved cutter 22 proximally along perforations 20, thus cutting (or "peeling") pod 14 open to release medical device 18.

Pod 14 may include any of a number of different distal end configurations. In the embodiment shown, for example, peel-away pod 14 has an open distal end, and medical device 18 protrudes out of the distal end to form a blunt tip. In another embodiment, pod 14 may include a blunt tip that completely surrounds medical device 18. In some embodiments, a the tip of pod 14 may be flexible, to help facilitate advancement along a guidewire through a tortuous anatomical path. In another alternative embodiment, peel-away pod 14 may include a sharp or pointed tip to facilitate piercing through tissue, for example to facilitate piercing through tough connective tissue to deliver device 18 into a joint space.

Referring now to FIGS. 2A and 2B, another embodiment of a medical device delivery catheter 40 suitably includes a catheter body 58 and a pod 41, with pod 41 being adapted to house medical device 18. Pod 41 generally includes two opposed housing members 42, movably coupled at their proximal ends by a hinge 56 to enable pod 41 to open like a clam shell (FIG. 2B). Attached to one of housing members 42 is a guidewire tube 44 to allow catheter 40 to be advanced over a guidewire 46. Disposed over the distal end of pod 41 in FIG. 2A is a ring 48, coupled with a pull cord 50. A movable inner shaft 54 extends through catheter body 58 and is attached distally to a platform 52 for helping push medical device 18 out of the opened pod 41 (FIG. 2B).

Various alternative embodiments of catheter 40 may include a number of variations. For example, guidewire tube 44, in some embodiments, may be positioned on the inside of pod 41, may extend onto catheter body 58 or may be disposed entirely on catheter body 58 and not on pod 41. Similarly, pull cord 50 may be disposed inside pod 41 and catheter body 58 in some embodiments. Inner shaft 54 and platform 52 are optional features, which are not necessarily included in all embodiments. In an alternative embodiment, platform 52 is attached via a spring to the proximal end of the inside of pod 41, such that platform 52 is spring-loaded and automatically springs forward upon release of medical device 18 from pod 41. Any suitable hinge 56, or multiple hinges, may be substituted. In alternative embodiments, pod 41 may open by curving outward due to shape-memory or spring-loaded materials rather than via a hinge. Other closure devices may also be substituted for ring 48, such as a closure sleeve, pin, movable clamp or the like. Housings 42 may be either rigid or flexible and may be made of any suitable material or combination of materials. In some embodiments, the outer diameter of pod 41 is greater than the outer diameter of catheter body 58, as in FIGS. 2A and 2B. In alternative embodiments, the outer diameters may be the same. Thus, various embodiments of medical device delivery catheter 40 may have any of a number of different configurations and features, without departing from the scope of the present invention.

In use, delivery catheter 40 is positioned in a desired location for delivering medical device 18, such as in the stomach and possibly extending across the pyloric valve into the duodenum. Advancement to a desired location may be facilitated by incorporating one or more radiopaque markers or materials into catheter 40 and/or by including one or more depth markings on the outer surface of a proximal portion of catheter body 58 to help the user determine how far catheter 40 has been advanced into the body. Once pod 41 and medical device 18 are in a desired location, pull cord 50 is pulled proximally by a user at the proximal end of catheter 40, thus causing ring to move proximally down pod 41 (solid-tipped arrows). Medical device 18 is constrained in a compressed configuration within pod 41, such that when ring 48 is moved proximally (FIG. 2B), medical device 18 springs/expands into an unconstrained, expanded configuration, thus pushing apart housing members 42, which separate easily due to hinge 56. Medical device 18 is thus released from pod 41. To further urge medical device 18 out of pod 41, inner shaft 54 may be advanced by the user to push medical device 18 forward with platform 52. Using this method, medical device 18 may be placed such that a distal portion 21 resides within the duodenum, a connection portion 19 resides across the pyloric valve, and a proximal portion 17 resides within the stomach. The distal portion 21 and proximal portion 17 are typically the expandable portions constrained within pod 41 when it is closed and that push pod 41 open when ring 48 or other constraining device is removed. Once medical device 18 is released, housing members 42 close naturally as delivery catheter 40 is withdrawn from the body.

Figure 3A:
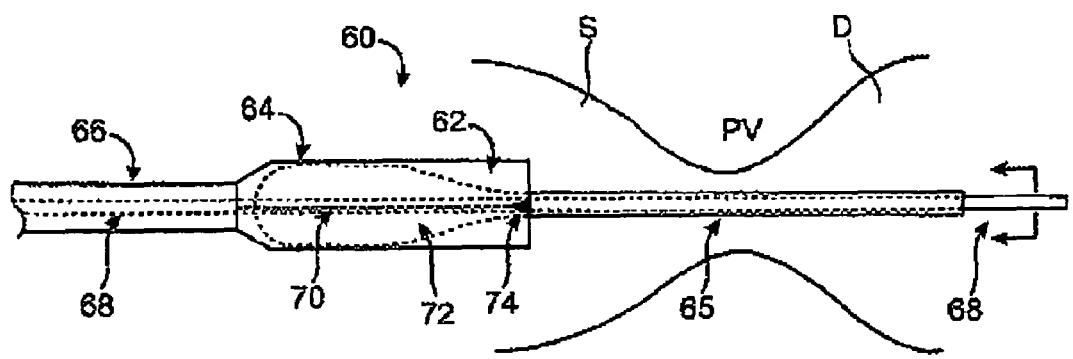
FIGS. 3A-3C are side views of a distal end of a medical device delivery catheter having a pod and a retractable inner shaft, the figures illustrating a method of medical device delivery, according to one embodiment of the present invention.
Figure 3B:
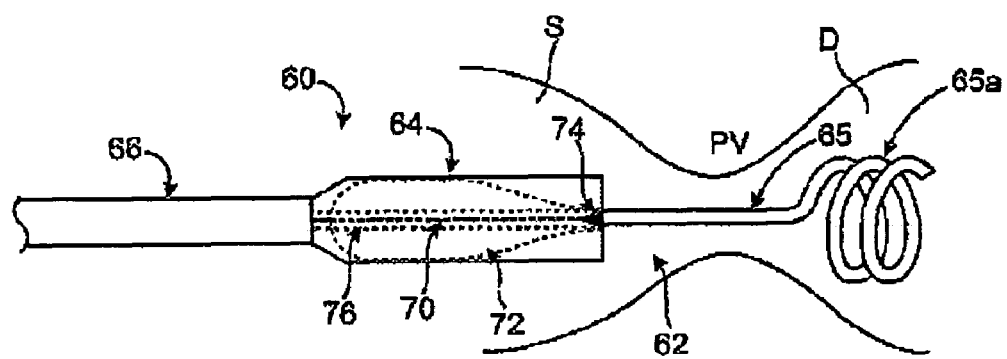
Figure 3C:
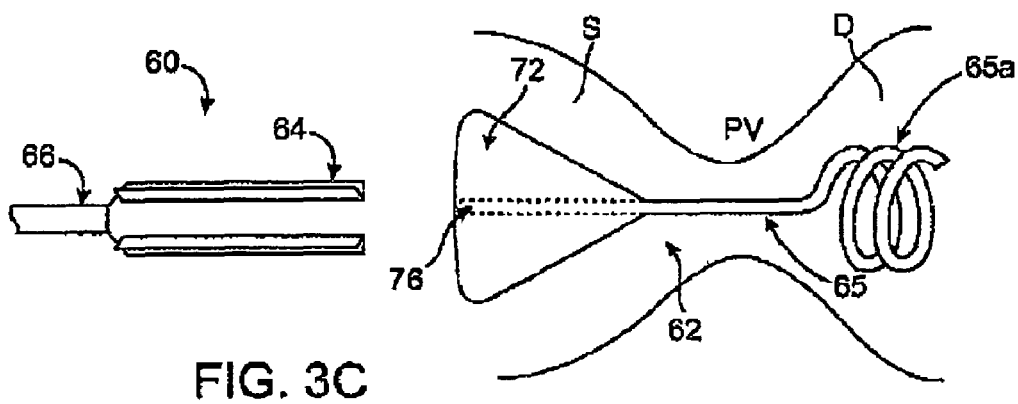

Referring now to FIGS. 3A-3C, in an alternative embodiment, a medical device delivery catheter 60 suitably includes a catheter body 66, a pod 64 attached to the distal end of catheter body 66, and a retractable inner shaft 68, extending through catheter body 66 and pod 64, and beyond the distal end of pod 64. Pod 64 includes a perforated line 70 and a cutter 74. Medical device 62, in this embodiment, includes an expandable proximal portion 72, and a distal portion 65, which includes a shape memory distal end 65. As shown in FIGS. 3B and 3C, proximal portion 72 includes a central lumen 76, through which inner shaft 68 may pass.

With reference to FIG. 3A, in use, delivery catheter 60 is positioned such that pod 64 resides within a patient's stomach S and inner shaft 68 with distal portion 65 of medical device 62 extends at least partially across the pyloric valve PV, and sometimes into the duodenum D, as shown. When catheter 60 and device 62 are in a desired location for deployment, which may be confirmed with one or more radiopaque marking on catheter 60 and/or device 62, and/or with depth markings on the outer surface of catheter body 66, inner shaft is retracted 68 (solid-tipped arrows). As illustrated in FIG. 3B, when inner shaft 68 is removed from distal portion 65, shape memory distal end 65a deforms from its straight, undeployed shape to its deployed shape, which in this case is a helical shape. Other shapes, such as a round or elliptical ball-like shape, an hourglass shape, a curled snail-like shape or the like may be used in alternative embodiments. Distal end 65a may suitably be made of any shape-memory, super-elastic material, spring-loaded, or other resilient material to allow it to move from the undeployed to deployed configuration. Generally, distal end 65a in its deployed configuration is designed to reside within a proximal portion of the duodenum D and to prevent its passage through the pyloric valve PV, back into the stomach S.

To deploy proximal portion 72 of medical device 62, pod 64 is cut (or torn, split or peeled, in various embodiments) along perforated line 70, using cutter 74. As shown in FIG. 3C, proximal portion 72 expands upon release from pod 64, thus assuming its deployed, expanded configuration, which causes it to remain in the stomach S and prevents it from crossing the pyloric valve PV into the duodenum D. Rotational orientation of medical device 62 about the long axis of catheter 60 may often be important to achieve a desired delivery. Thus, in some embodiments, the orientation of perforated line 70, and thus the side on which pod 64 opens, is configured to achieve a desired, and controlled, rotational orientation of medical device 62 upon delivery. Delivery catheter 60 may then be withdrawn, leaving medical device 62 in place within the stomach S, crossing the pyloric valve PV into the duodenum D.

Various embodiments of delivery catheter 60 may include additional features to enhance and/or facilitate delivery of medical device 62. For example, rotational orientation of inner shaft 68 with respect to medical device 62 may be controlled in some embodiments by "keying" device 62 to shaft 68. The keying function may be achieved by providing catheter 60 with a non-circular lumen (e.g., square, triangle, slot, etc.) keyed to a non-circular cross-sectional shape of device 62. In an alternative embodiment, device 62 may engage shaft 68 via a keyed anchor disposed along the length of device 62 (or in multiple locations). In one embodiment, an anchor is cast in the distal tip of device 62. The anchor may have a slot in which shaft 68 engages. In some embodiments, shaft 68 may also include one or more shape-memory or super-elastic materials, to counteract the restorative forces of medical device 62 in its constrained configuration.

Figure 4:
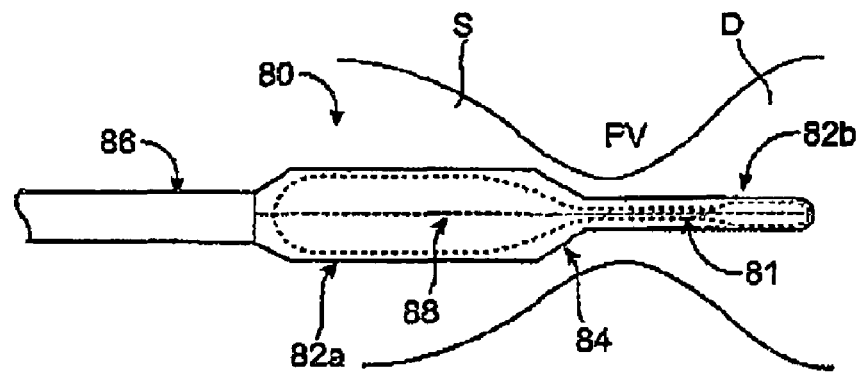
FIG. 4 is a side view of a distal end of a medical device delivery catheter having a pod with a stepped diameter, according to one embodiment of the present invention.

Referring now to FIG. 4, in one embodiment, a medical device delivery catheter 80 includes a catheter body 86 and a pod 82, which includes a wider proximal portion 82a, a narrower distal portion 82b, and a step-off 84 between the two. Pod 82 may open via perforations 88 or, in alternative embodiment, any other suitable means as described above. Distal portion 82b is configured and sized such that it can be advanced through the pyloric valve PV to position its distal end in the duodenum D. Step-off 84 is configured and sized such that it will not move through the pyloric valve PV. Thus, pod 82 is configured to allow a user to advance delivery catheter 80 partially through the pyloric valve to release a medical device 81 in a location spanning the valve. When delivery catheter 80 is sufficiently advanced, step-off 84 bumps up against the pyloric valve PV, such that the user can feel the abutment and knows catheter 80 is sufficiently advanced. Medical device 81 is then deployed in the desired location spanning the valve. In an alternative embodiment (not shown) the medical device itself, rather than the pod, includes a step-off in diameter to allow partial, but not complete, passage through the pyloric valve PV.

Figure 5:
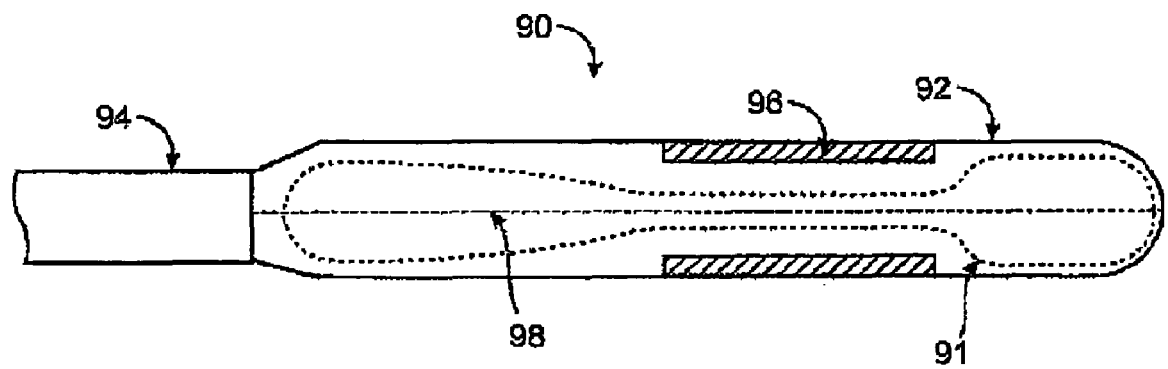
FIG. 5 is a side view of a distal end of a medical device delivery catheter having a pod with reinforcing side-wall members, according to one embodiment of the present invention.

In a number of embodiments, and with reference now to FIG. 5, medical device delivery catheter 90 includes a catheter body 94 and a pod 92 having one or more support members 96 disposed along its inner wall and one or more sets of perforations 98. Support members 96, for example, may be elongate, curved, horseshoe-shaped or otherwise configured pieces of silicone molded or attached to the wall via adhesive. In alternative embodiments, support members 96 may be attached with stitching or case into pod 92. In still further embodiments, support members 96 may be biodegradable. Support members 96 are generally configured to help stabilize pod 92 and prevent it from kinking or bending in an area in which a narrower portion of a medical device 91 is disposed. In other embodiments, support members 96 may be embedded in the wall of pod 92, and may include other materials such as metal.

Figure 7A:
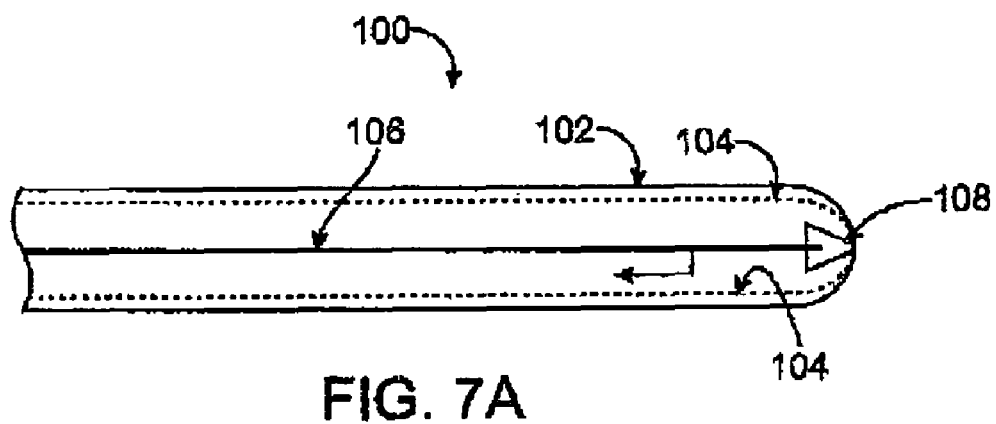
FIGS. 7A-7C are side views of a peel-away distal pod of a medical device delivery catheter, illustrating a method for peeling the pod, according to one embodiment of the present invention.
Figure 7B:
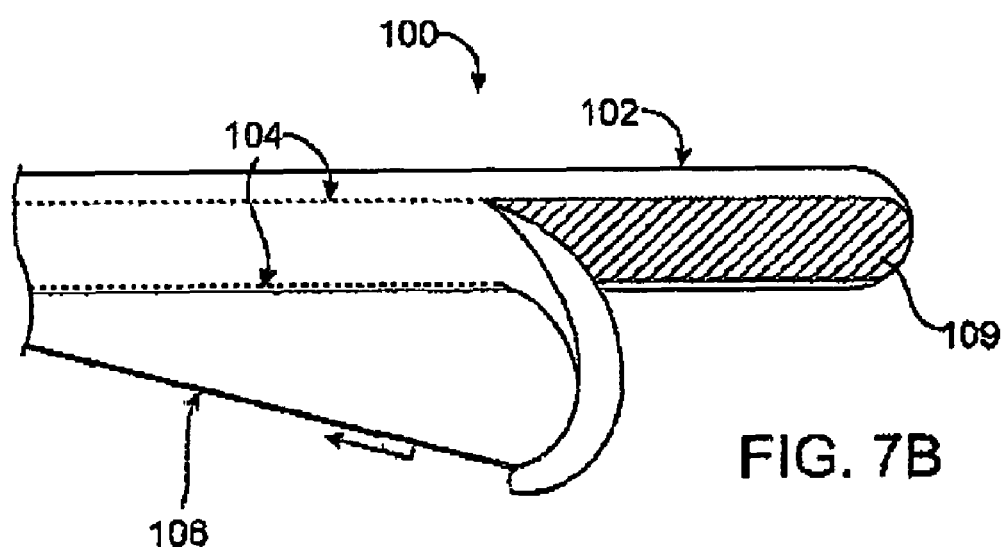
Figure 7C:
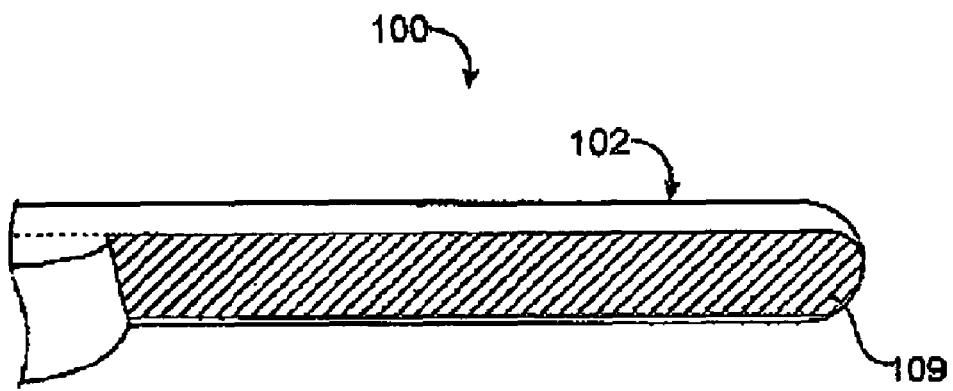

Referring now to FIGS. 7A-7C, another embodiment of a medical device delivery catheter 100 is shown, and a method for opening a pod 102 is illustrated. Pod 102 includes two sets of perforations 104, and a cord 106 extends along pod 102 and is attached at its distal end via an attachment member 108. When cord 106 is pulled proximally (solid-tipped arrow), a portion of pod 102 peels away, as shown in FIG. 7B, thus exposing the interior 109 of pod 102. Typically, a medical device (not shown) is housed in interior 109 and is thus released when pod 102 is peeled. As cord 106 is pulled farther proximally (solid-tipped arrow), pod 102 peels open further, as in FIG. 7C. In various embodiments, pod 102 may have any of a number of various perforations, slits, holes, thin material portions or the like to allow for peeling, tearing, cutting or other means for opening pod 102.

Although the above is a complete and accurate description of the invention, any of a number of variations, additions and the like may be made to the embodiments described without departing from the scope of the invention. For example, devices and methods described above may be used to treat any suitable condition or perform any suitable function within the gastrointestinal tract. Therefore, the foregoing description is provided primarily for exemplary purposes and should not be interpreted to limit the scope of the invention as it is defined in the following claims.

What is claimed is:

1. Apparatus for delivering a medical device to a location in a patient's body the apparatus comprising:
    an elongate catheter body having a proximal end and a distal end;
    a pod coupled with the distal end of the catheter body and adapted to house the medical device during delivery to the location and to open to release the medical device; and
    at least one distal actuator coupled with at least one of the pod and the medical device, the distal actuator adapted to promote opening of the pod,
    wherein the pod comprises a material disposed over the medical device, the material adapted to tear or peel to open the pod, and
    wherein the material comprises a shape-memory material adapted to curl inward after the material is torn or peeled.

2. Apparatus for delivering a medical device to a location in a patient's body, the apparatus comprising:
    an elongate catheter body having a proximal end and a distal end;
    a pod coupled with the distal end of the catheter body and adapted to house the medical device during delivery to the location and to open to release the medical device; and
    at least one distal actuator coupled with at least one of the pod and the medical device, the distal actuator adapted to promote opening of the pod,
    wherein the pod comprises a material disposed over the medical device, the material adapted to tear or peel to open the pod, and
    wherein the material includes a plurality of apertures disposed along opposite ends, the apparatus further comprising a cord for passing through the apertures to maintain the material over the medical device, wherein removing the cord causes the pod to open.

3. Apparatus for delivering a medical device to a location in a patient's body, the apparatus comprising:
    an elongate catheter body having a proximal end and a distal end;
    a pod coupled with the distal end of the catheter body and adapted to house the medical device during delivery to the location and to open to release the medical device; and
    at least one distal actuator coupled with at least one of the pod and the medical device, the distal actuator adapted to promote opening of the pod,
    wherein the pod comprises a material disposed over the medical device, the material adapted to tear or peel to open the pod, and
    wherein the distal actuator comprises a pressure input member for introducing positive pressure into the pod to cause the material to burst.

4. Apparatus for delivering a medical device to a location in a patient's body, the apparatus comprising:
    an elongate catheter body having a proximal end and a distal end;
    a pod coupled with the distal end of the catheter body and adapted to house the medical device during delivery to the location and to open to release the medical device; and at least one distal actuator coupled with at least one of the pod and the medical device, the distal actuator adapted to promote opening of the pod,
    wherein the pod comprises a material disposed over the medical device, the material adapted to tear or peel to open the pod, and
    wherein the distal actuator comprises an inflation device coupled with the medical device for inflating the medical device to cause the device to expand and rupture the material.

5. Apparatus for delivering a medical device to a location in a patient's body, the apparatus comprising:
    an elongate catheter body having a proximal end and a distal end;
    a pod coupled with the distal end of the catheter body and adapted to house the medical device during delivery to the location and to open to release the medical device; and at least one distal actuator coupled with at least one of the pod and the medical device, the distal actuator adapted to promote opening of the pod, further comprising a retractable inner shaft extending axially through the housing, wherein the medical device includes at least one lumen to allow the medical device to reside over the inner shaft during delivery, and wherein retracting the inner shaft releases at least part of the medical device, wherein the retractable shaft extends beyond a distal end of the pod, wherein retracting the shaft releases a distal portion of the medical device, and wherein opening the pod releases a proximal portion of the medical device.

6. Apparatus for delivering a medical device to a location in a patient's body, the apparatus comprising:

an elongate catheter body having a proximal end and a distal end;

a pod coupled with the distal end of the catheter body and adapted to house the medical device during delivery to the location and to open to release the medical device; and at least one distal actuator coupled with at least one of the pod and the medical device, the distal actuator adapted to promote opening of the pod, wherein the pod comprises:

at least two opposed housing members for releasably housing the medical device; and at least one hinge for movably coupling the housing members, wherein the housing members are adapted to move about the hinge(s) to cause the pod to open.

7. Apparatus as in claim 6, wherein the housing members comprise a material selected from the group consisting of a polymer, a ceramic, a metal, a composite and a biological material.

8. Apparatus as in claim 6, wherein the hinge is selected from the group consisting of a flexible material hinge, a living hinge, a pin joint and a universal joint.

9. Apparatus as in claim 6, wherein at least part of each housing member comprises at least one of a shape-memory material, a super-elastic material and a spring loaded material, and wherein the housing members are preformed to move away from one another when released from constraint.

10. Apparatus as in claim 9, wherein the distal actuator is adapted to releasably hold the pod in a closed configuration and, upon activation, to release the pod to allow it to assume the open configuration.

11. Apparatus as in claim 10, wherein the distal actuator is selected from the group comprising a ring, a retractable sleeve, a tearable sleeve, a pin and a clamp.

12. Apparatus as in claim 6, further comprising at least one spring disposed between the housing members to urge them apart.

13. Apparatus as in claim 6, wherein the distal actuator comprises at least one movable holder disposed about the housing members, wherein the holder is movable from a first position to hold the housing members together to a second position to allow the housing members to move apart.

14. Apparatus as in claim 13, wherein the holder is movable from the second position to the first position to move the housing members back together.

15. Apparatus as in claim 13, wherein the actuator further comprises a wedge for urging the housing members apart when the holder is moved from the first to the second position.

16. Apparatus as in claim 13, wherein the holder comprises at least one ring disposed around the housing members, and wherein the ring in the first position is disposed near a distal end of the pod and the ring in the second position is disposed near a proximal end of the pod.

17. Apparatus as in claim 13, wherein the holder comprises a sleeve movably disposed over the housing members.

18. Apparatus for delivering a medical device to a location in a patient's body, the apparatus comprising:

an elongate catheter body having a proximal end and a distal end;

a pod coupled with the distal end of the catheter body and adapted to house the medical device during delivery to the location and to open to release the medical device; and at least one distal actuator coupled with at least one of the pod and the medical device, the distal actuator adapted to promote opening of the pod, wherein the pod includes an open distal end, and wherein a distal end of the medical device extends out of the open distal end of the pod to form a flexible tip.

19. Apparatus for delivering a medical device to a location in a patient's body, the apparatus comprising:

an elongate catheter body having a proximal end and a distal end;

a pod coupled with the distal end of the catheter body and adapted to house the medical device during delivery to the location and to open to release the medical device; and at least one distal actuator coupled with at least one of the pod and the medical device, the distal actuator adapted to promote opening of the pod, wherein the pod comprises a distal tip, and wherein the tip comprises a rigid, pointed tip adapted to pierce through tissue.

20. Apparatus for delivering a medical device to a location in a patient's body, the apparatus comprising:

an elongate catheter body having a proximal end and a distal end;

a pod coupled with the distal end of the catheter body and adapted to house the medical device during delivery to the location and to open to release the medical device; and at least one distal actuator coupled with at least one of the pod and the medical device, the distal actuator adapted to promote opening of the pod, wherein the pod comprises a distal tip, and wherein the tip comprises a flexible nose having at least one aperture or lumen for accepting a guidewire.

21. Apparatus for delivering a medical device to a location in a patient's body, the apparatus comprising:

an elongate catheter body having a proximal end and a distal end;

a pod coupled with the distal end of the catheter body and adapted to house the medical device during delivery to the location and to open to release the medical device; and at least one distal actuator coupled with at least one of the pod and the medical device, the distal actuator adapted to promote opening of the pod, further comprising at least one support member disposed along at least part of a length of the pod for reducing bending of the pod, wherein the at least one support member comprises multiple support members disposed along an inner surface of the pod.

22. Apparatus as in claim 21, wherein the support members comprise silicone.

23. Apparatus for delivering a medical device to a location in a patient's body, the apparatus comprising:
    an elongate catheter body having a proximal end and a distal end; and
    a pod coupled with the distal end of the catheter body and adapted to house the medical device during delivery to the location and to open to release the medical device,
    wherein the pod is adapted to automatically open after being positioned in the location,
    wherein the pod comprises a material disposed over the medical device, and
    wherein at least part of the material is biodegradable.

24. Apparatus as in claim 23, the pod further comprising at least two opposed housing members disposed within the material, wherein the housing members automatically move apart to cause the pod to open when the material at least partially degrades.

25. Apparatus as in claim 23 or 24, wherein the location is a stomach of the patient, and wherein at least part of the material is rapidly biodegradable in the stomach.

26. Apparatus as in claim 23, wherein the pod comprises a material disposed over the medical device, and wherein at least part of the material degrades upon reaching a temperature present at a desired delivery location.

* * * * *